(12) United States Patent
Furman et al.

(10) Patent No.: US 6,892,013 B2
(45) Date of Patent: May 10, 2005

(54) FIBER OPTICAL ILLUMINATION SYSTEM

(75) Inventors: Dov Furman, Rehovot (IL); Gad Neumann, Rehovot (IL); Noam Dotan, Givataim (IL)

(73) Assignee: Negevtech Ltd., Rehovot (IL)

( * ) Notice: Subject to any disclaimer, the term of this patent is extended or adjusted under 35 U.S.C. 154(b) by 98 days.

(21) Appl. No.: 10/345,096

(22) Filed: Jan. 15, 2003

(65) Prior Publication Data

US 2004/0136665 A1 Jul. 15, 2004

(51) Int. Cl.$^7$ ................................................ G02B 6/04
(52) U.S. Cl. ...................................................... 385/115
(58) Field of Search ................................. 385/115, 120, 385/121, 901; 362/554, 566

(56) References Cited

U.S. PATENT DOCUMENTS

| | | | |
|---|---|---|---|
| 3,598,467 A | * | 8/1971 | Pearson ........................ 359/27 |
| 4,011,403 A | * | 3/1977 | Epstein et al. .............. 348/370 |
| 4,247,203 A | | 1/1981 | Levy et al. .................. 356/398 |
| 4,347,001 A | | 8/1982 | Levy et al. .................. 356/398 |
| 4,360,372 A | * | 11/1982 | Maciejko ...................... 65/402 |
| 4,378,159 A | | 3/1983 | Galbraith ..................... 356/237 |
| 4,556,317 A | | 12/1985 | Sandland et al. ........... 356/237 |
| 4,579,455 A | | 4/1986 | Levy et al. .................. 356/394 |
| 4,597,665 A | | 7/1986 | Galbraith et al. ........... 356/237 |
| 4,601,576 A | | 7/1986 | Galbraith .................... 356/237 |
| 4,618,938 A | | 10/1986 | Sandland et al. ........... 364/552 |
| 4,639,587 A | | 1/1987 | Chadwick et al. .......... 250/201 |
| 4,644,172 A | | 2/1987 | Sandland et al. ........... 250/548 |
| 4,734,923 A | | 3/1988 | Frankel et al. ................ 378/34 |
| 4,760,265 A | | 7/1988 | Yoshida et al. .......... 250/492.2 |

(Continued)

FOREIGN PATENT DOCUMENTS

WO    WO 00/70332    11/2000

OTHER PUBLICATIONS

Patent Abstracts of Japan, vol. 17, No. 613, Jul, 1993 & JP 05 190421.
Patent Abstracts of Japan, vol. 1996, No. 10, Jun., 1996 & JP 08 154210.
Patent Abstracts of Japan, vol. 1999, No. 04, Jan.,1999 & JP 11 014357.
Patent Abstracts of Japan, vol. 1997, No. 03, Nov.,1996 & JP 08 292361.
"Machine Vision and Applications", 1998 1:205–221, by IBM Scientists Byron E. Dom, et al.
"Speckle Reduction with Virtual Incoherent Laser Illumination Using Modified Fiber Array", by Dingel et al., published in Optik, vol. 94, No. 3, pp. 132–136, 1993.
"Speckle Reduction in Pulsed–Laser Photography " by D. Kohler et al., published in Optics Communications, vol. 12, No. 1, pp. 24–28, Sep. 1974.
"Speckle Reduction" by T.S. McKecknie, pp. 123–170 in Topics in Applied Physics, vol. 9, Laser Speckle and Related Phenomena, edited by J.C. Dainty Springer Verlag 1984.

*Primary Examiner*—Rodney Bovenick
*Assistant Examiner*—Mike Stahl
(74) *Attorney, Agent, or Firm*—Ladas & Parry LLP

(57) ABSTRACT

A fiber optical illumination delivery system, which is effective in reducing the effects of source coherence. The system preferably utilizes either a single bundle of optical fibers, or serial bundles of optical fibers. In the single bundle embodiment, the differences in optical lengths between different fibers of the bundle is preferably made to be equal to even less than the coherence length of the source illumination. In the serial bundle embodiment, the fibers in the other bundle are arranged as groups of fibers of the same length, and it is the difference in lengths of these groups which is made equal to, or even more preferably, less than the overall difference in length between the shortest and the longest fibers in the other bundle. Both of these fiber systems enable construction of illumination systems delivering a higher level of illumination, but without greatly affecting the coherence breaking abilities of the system, thus enabling a generally more applicable system to be constructed.

14 Claims, 5 Drawing Sheets

U.S. PATENT DOCUMENTS

| | | | |
|---|---|---|---|
| 4,766,324 A | 8/1988 | Saadat et al. | 250/563 |
| 4,845,558 A | 7/1989 | Tsai et al. | 358/106 |
| 4,877,326 A | 10/1989 | Chadwick et al. | 326/394 |
| 4,898,471 A | 2/1990 | Stonestrom | 356/394 |
| 4,967,095 A | 10/1990 | Berger et al. | 250/572 |
| 4,969,198 A | 11/1990 | Batchelder et al. | 382/8 |
| 5,008,743 A | 4/1991 | Katzir et al. | 358/101 |
| 5,029,975 A * | 7/1991 | Pease | 385/120 |
| 5,056,765 A | 10/1991 | Brandstater | 269/20 |
| 5,058,982 A | 10/1991 | Katzir | 385/33 |
| 5,076,692 A | 12/1991 | Neukermans et al. | 356/538 |
| 5,112,129 A | 5/1992 | Davidson et al. | 356/359 |
| 5,153,668 A | 10/1992 | Katzir et al. | 356/237 |
| 5,264,912 A | 11/1993 | Vaught et al. | 356/237 |
| 5,267,017 A | 11/1993 | Uritsky et al. | 356/375 |
| 5,381,004 A | 1/1995 | Uritsky et al. | 250/307 |
| 5,422,724 A | 6/1995 | Kinney et al. | 356/375 |
| 5,537,669 A | 7/1996 | Evans et al. | 382/141 |
| 5,586,058 A | 12/1996 | Aloni et al. | 364/552 |
| 5,604,585 A | 2/1997 | Johnson et al. | 356/237 |
| 5,608,155 A | 3/1997 | Ye et al. | 73/28.01 |
| 5,619,429 A | 4/1997 | Aloni et al. | 364/552 |
| 5,619,588 A | 4/1997 | Yolles et al. | 382/149 |
| 5,659,172 A | 8/1997 | Wagner et al. | 250/307 |
| 5,699,447 A | 12/1997 | Alumot et al. | 382/145 |
| 5,797,317 A | 8/1998 | Lahat et al. | 101/127.1 |
| 5,798,829 A | 8/1998 | Vaez-Iravani | 356/237 |
| 5,822,055 A | 10/1998 | Tsai et al. | 356/237 |
| 5,825,482 A | 10/1998 | Nikoonahad et al. | 356/237 |
| 5,864,394 A | 1/1999 | Jordan, III et al. | 356/237 |
| 5,883,710 A | 3/1999 | Nikoonahad et al. | 356/237.2 |
| 5,892,579 A | 4/1999 | Elyasaf et al. | 356/239.8 |
| 5,907,628 A | 5/1999 | Yolles et al. | 382/149 |
| 5,912,735 A | 6/1999 | Xu | 356/345 |
| 5,917,588 A | 6/1999 | Addiego | 356/237 |
| 5,939,647 A | 8/1999 | Chinn et al. | 73/864.71 |
| 5,970,168 A | 10/1999 | Montesanto et al. | 382/149 |
| 5,982,921 A | 11/1999 | Alumot et al. | 382/145 |
| 5,991,699 A | 11/1999 | Kulkarni et al. | 702/83 |
| 6,020,957 A | 2/2000 | Rosengaus et al. | 356/237.4 |
| 6,021,214 A | 2/2000 | Evans et al. | 382/141 |
| 6,064,517 A | 5/2000 | Chuang et al. | 359/364 |
| 6,075,375 A | 6/2000 | Burkhart et al. | 324/758 |
| 6,078,386 A | 6/2000 | Tsai et al. | 356/237.1 |
| 6,099,596 A | 8/2000 | Li et al. | 29/25.01 |
| 6,122,046 A | 9/2000 | Almogy | 356/237.2 |
| 6,124,924 A | 9/2000 | Feldman et al. | 356/153 |
| 6,169,282 B1 | 1/2001 | Maeda et al. | 250/310 |
| 6,172,349 B1 | 1/2001 | Katz et al. | 250/201.3 |
| 6,175,645 B1 | 1/2001 | Elysaf et al. | 382/147 |
| 6,175,646 B1 | 1/2001 | Schemmel et al. | 382/149 |
| 6,178,257 B1 | 1/2001 | Alumot et al. | 382/145 |
| 6,208,411 B1 | 3/2001 | Vaez-Iravani | 356/237.2 |
| 6,208,750 B1 | 3/2001 | Tsadka | 382/145 |
| 6,215,551 B1 | 4/2001 | Nikoonahad et al. | 356/237.2 |
| 6,236,454 B1 | 5/2001 | Almogy | 356/237.3 |
| 6,256,093 B1 | 7/2001 | Ravid et al. | 356/237.2 |
| 6,267,005 B1 | 7/2001 | Samsavar et al. | 73/105 |
| 6,268,093 B1 | 7/2001 | Kenan et al. | 430/30 |
| 6,268,916 B1 | 7/2001 | Lee et al. | 356/369 |
| 6,271,916 B1 | 8/2001 | Marxer et al. | 356/237.3 |
| 6,274,878 B1 | 8/2001 | Li et al. | 250/548 |
| 6,288,780 B1 | 9/2001 | Fairley et al. | 356/237.1 |
| 6,317,514 B1 | 11/2001 | Reinhorn et al. | 382/147 |
| 6,347,173 B1 * | 2/2002 | Suganuma et al. | 385/115 |
| 6,360,005 B1 | 3/2002 | Aloni et al. | 382/148 |
| 6,361,910 B1 | 3/2002 | Sarig et al. | 430/30 |
| 6,369,888 B1 | 4/2002 | Karpol et al. | 356/237.5 |
| 2002/0067478 A1 | 6/2002 | Karpol et al. | 356/237.5 |

* cited by examiner

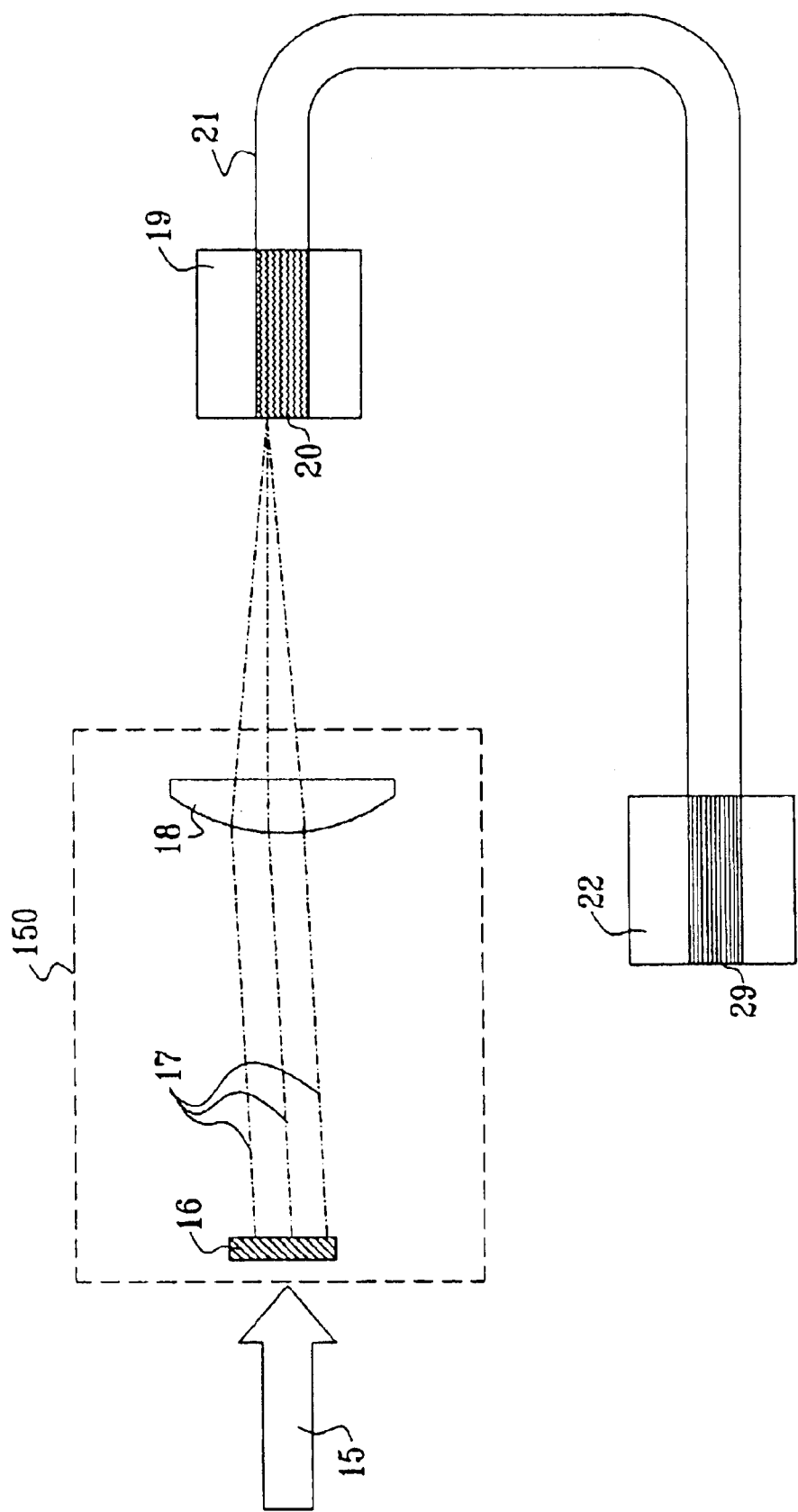

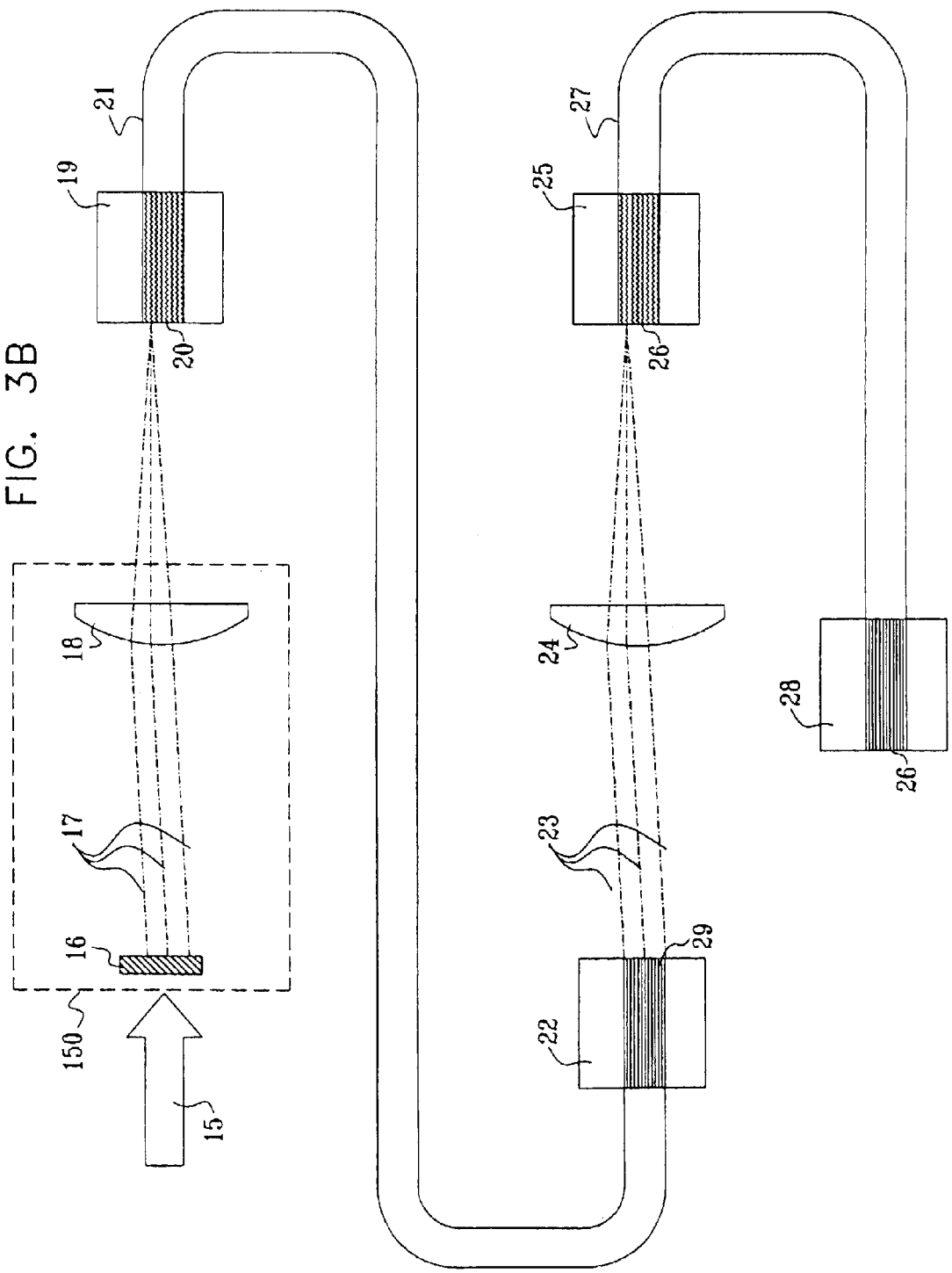

FIBER OPTICAL ILLUMINATION SYSTEM

FIELD OF THE INVENTION

The present invention relates to the field of fiber optical systems for illumination of objects to be imaged, and especially to ways of reducing speckle effects arising from the coherence of the illumination source used.

BACKGROUND OF THE INVENTION

The nature of a laser beam, and especially its coherent nature, presents a number of problems when used as an illuminating source in applications requiring a uniform illuminating flux over the inspected area, such as is required, for instance, in a wafer inspection system:
(i) Interference of light in the illumination optics creates non-uniformity in the illumination field.
(ii) Interference of the illuminated light by the structured pattern on the wafer creates artifacts in the image.
(iii) Surface roughness creates speckle, that generates non-uniformity in the image.
(iv) The laser beam itself is generally not uniform. Using the laser beam directly as a light source creates non-uniform illumination.

In order to overcome items (i) to (iii) above, the effects of the coherent nature of the laser beam must be reduced and preferably eliminated completely. This process is known as coherence breaking.

There are two definitions related to the coherence of a laser beam:
(a) Spatial coherence, which is the phase relation between each spatial point in the laser beam spot. This allows different points in the spot to interact with each other in a destructive or constructive manner when the spot is illuminating a cyclic pattern or a rough surface. This quality depends mainly on the mode of the beam. For instance in the basic mode ($TEM_{00}$) the spatial coherence is defined by the Gaussian profile of the beam.
(b) Temporal coherence, which is a measure of the time or the transit distance (the time multiplied by the speed of light in the medium concerned) over which the phase of the beam can be defined. This parameter depends on the type of laser and its spectral bandwidth. Thus, for instance, for the second harmonic of a Nd:YAG laser at 532 nm, the coherence length is about 8 mm in free space.

There are a number of methods described in the prior art for overcoming coherence effects in using laser illumination. Reference is made to the articles "Speckle Reduction" by T. S. McKecknie, pp. 123–170 in Topics in Applied Physics, Vol. 9, Laser Speckle and Related Phenomena, edited by J. C. Dainty, Springer Verlag (1984), "Speckle reduction in pulsed-laser photography" by D. Kohler et al., published in Optics Communications, Vol. 12, No. 1, pp. 24–28, (September 1974) and "Speckle reduction with virtual incoherent laser illumination using modified fiber array" by B. Dingel et al., published in Optik, Vol. 94, No. 3, pp. 132–136, (1993), and to U.S. Pat. No. 6,369,888 to A. Karpol et al., for "Method and Apparatus for Article Inspection including Speckle Reduction", the disclosures of all of which are herein incorporated by reference, each in its entirety.

The above-mentioned prior art solutions to the problem of coherence breaking variously have specific disadvantages, and it is an object of the present invention to attempt to overcome some of these advantages.

SUMMARY OF THE INVENTION

The present invention seeks to provide a new fiber optical illumination delivery system, which is effective in reducing the speckle effects arising from source coherence. The system preferably utilizes either a single bundle of optical fibers, or serial bundles of optical fibers, according to the various preferred embodiments of the present invention. The single bundle embodiment differs from prior art systems in that the differences in optical lengths between different fibers of the bundle is preferably made to be equal to or more preferably less than the coherence length of the source illumination. This preferred embodiment enables construction of an illumination system delivering a higher level of illumination, but without greatly affecting the coherence breaking abilities of the system, thus enabling a generally more applicable and cost-effective system to be constructed.

The serial bundle embodiment differs from prior art systems in that in the bundle comprising the fibers, where in the prior art systems, the differences in lengths of the fibers therein is made equal to the overall difference in length between the shortest and the longest fibers in the other bundle, according to a preferred embodiment of this invention, there are arranged groups of fibers of the same length, and it is the difference in lengths of these groups which is made equal to, or even more preferably, less than the overall difference in length between the shortest and the longest fibers in the other bundle. This preferred embodiment also enables construction of an illumination system delivering a higher level of illumination, but without greatly affecting the coherence breaking abilities of the system, thus enabling a generally more applicable system to be constructed.

There is thus provided in accordance with a preferred embodiment of the present invention, an optical system for reducing the coherence of a beam for illumination of an object, comprising a source of at least partially coherent illumination, at least part of which has a characteristic coherence length, and at least one fiber optics bundle comprising a plurality of optical fibers, at least some of which have differing optical lengths, at least some of the fibers of differing optical length having differences in optical lengths therebetween which are less than the characteristic coherence length.

In the above system, the source of at least partially coherent illumination may preferably be a laser source, and the coherent illumination may have spatial coherence or temporal coherence or both. To reduce spatial coherence, the plurality of optical fibers in the at least one fiber optics bundle are preferably randomly ordered. Furthermore, a diffusing element may be used for spatial mixing of the beam. The optical system may also comprise an optical element positioned such that it is operative to direct the illumination from any point of the beam into essentially each of the plurality of fibers.

According to yet another preferred embodiment of the present invention, in the above described optical system, the differences in optical lengths being less than the characteristic coherence length, results in a bundle having reduced transmission losses.

In accordance with still another preferred embodiment of the present invention, the illumination beam comprises pulses having a characteristic length, and the bundle is operative to stretch the length of the pulses.

There is further provided in accordance with still another preferred embodiment of the present invention, an optical system for reducing the coherence of a beam for illumination of an object, comprising a source of at least partially coherent illumination, at least part of the illumination having a characteristic coherence length, a first fiber optics bundle comprising a plurality of optical fibers, at least some of which have differing optical lengths, at least some of the fibers of differing optical length having differences in optical lengths therebetween which are less than the characteristic coherence length, and a second fiber optics bundle disposed serially with the first bundle, comprising a plurality of groups of optical fibers, each group of fibers comprising fibers of essentially the same length, and wherein at least some of the group of fibers have differing optical lengths, at least some of the groups of fibers having differences in optical lengths therebetween which are at least equal to the sum of all of the optical length differences of the fibers in the first bundle.

In the above-described embodiment, each of the groups may have essentially the same number of fibers, or alternatively and preferably, the number of fibers in each of the groups may increase according to the optical length of the group, and even more preferably, the number of fibers in each group may generally be proportional to the length of the group.

The bundles may be arranged serially such that the beam for illumination of the object is initially incident on the first bundle or alternatively and preferably, the beam for illumination of the object is initially incident on the second bundle. In either case, according to further preferred embodiments of this invention, an optical element is positioned between the bundles such that it is operative to direct illumination from any point of the output of the first bundle onto essentially each point of the input of the second bundle.

In the above system, the source of at least partially coherent illumination may preferably be a laser source, and the coherent illumination may have spatial coherence or temporal coherence or both. To reduce spatial coherence, the plurality of optical fibers in the at least one fiber optics bundle are preferably randomly ordered. Furthermore, a diffusing element may be used for spatial mixing of the beam.

In accordance with still a further preferred embodiment of the present invention, there is also provided a method of reducing the transmission loss in a fiber optical bundle for reducing the coherence of light transmitted therethrough, at least part of which light has a characteristic coherence length, the method comprising the steps of providing at least one fiber optical bundle comprising a plurality of optical fibers, at least some of which have differing optical lengths, and arranging the lengths of the plurality of optical fibers such that at least some of the fibers of differing optical lengths have differences in optical length therebetween generally less than the characteristic coherence length.

BRIEF DESCRIPTION OF THE DRAWINGS

The present invention will be understood and appreciated more fully from the following detailed description, taken in conjunction with the drawings in which;

FIG. 2 is a schematic drawing of a fiber optical delivery bundle, according to a preferred embodiment of the present invention, such as that used in FIG. 1;

FIGS. 3A to 3E schematically show various preferred embodiments of fiber bundle applications, according to further preferred embodiments of the present invention;

FIG. 3A is a graphical illustration of the transmission and the coherence reduction factor of a single fiber optical bundle, such as that shown in the embodiment of FIG. 1, as a function of fiber optical length difference divided by the coherence length of the source;

FIG. 3B is a schematic illustration of a double bundle fiber optical illumination system, according to a preferred embodiment of the present invention;

FIGS. 3C and 3D respectively illustrate schematically two embodiments of a first bundle of a double bundle illumination system, such as that of FIG. 3B, according to another preferred embodiment of the present invention, in which the bundle is made up of groups of fibers of the same length; and FIG. 3E is a schematic drawing of the second bundle of fibers of the preferred embodiment of FIG. 3B, in which each of the fibers is of a different optical length, the optical lengths preferably differing by the coherence length of the light source or less.

DETAILED DESCRIPTION OF PREFERRED EMBODIMENTS

Figure 1:
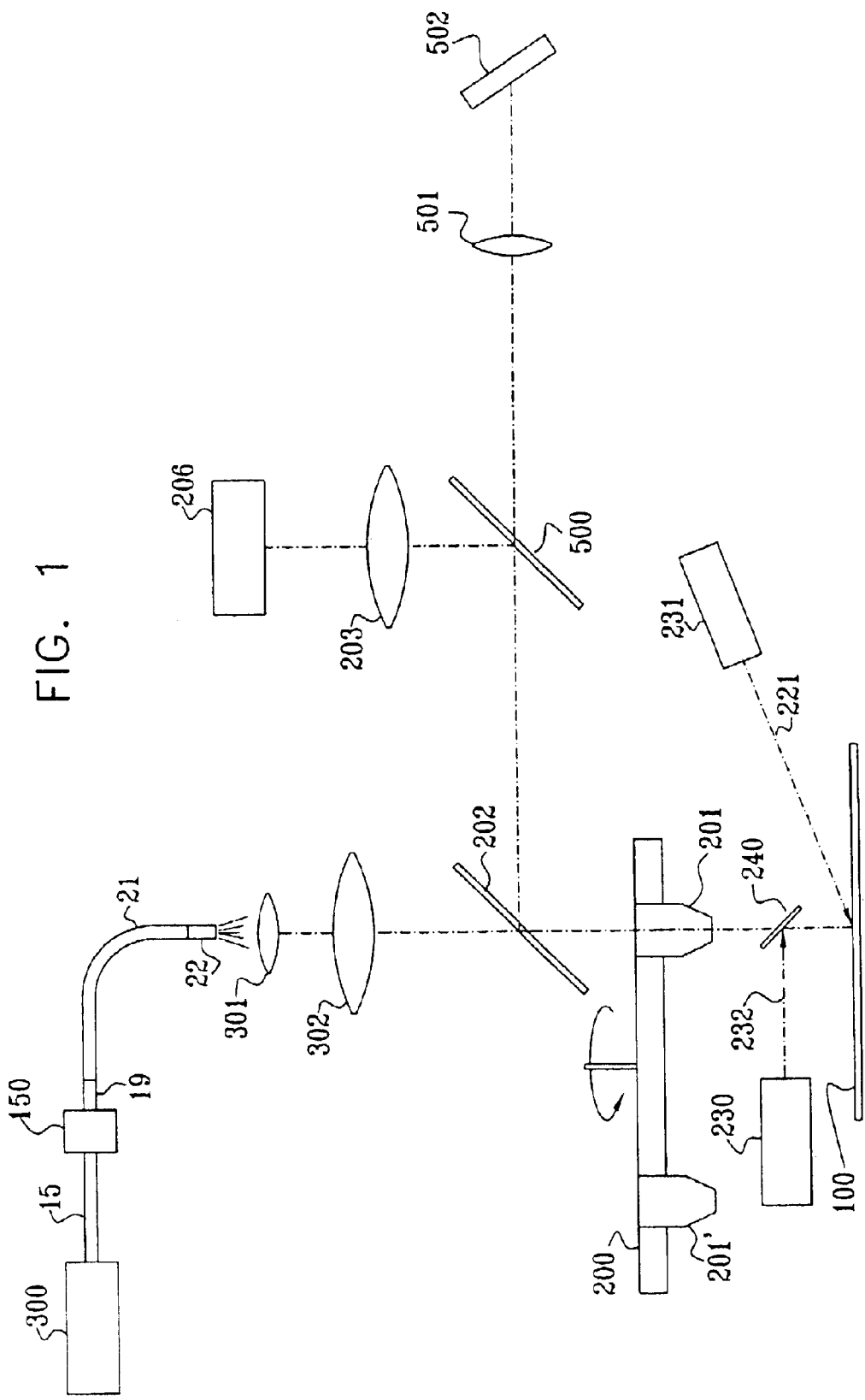
FIG. 1 is a schematic illustration of a bright field object inspection system, utilizing a laser source and a fiber optical delivery bundle, constructed and operative according to a preferred embodiment of the present invention.

Reference is now made to FIG. 1, which is an overall schematic side view of the complete illumination system of the defect detection apparatus, according to one preferred embodiment of the present invention. According to different preferred methods of operation, three alternative modes of illumination are provided: Bright Field (BF), Side-illuminated Dark Field (DF) and Orthogonal or Obscured Reflectance Dark Field (ODF). Each mode of illumination is used to detect different types of defects in different production process steps. For example in order to detect an embedded defect in a transparent layer, such as silicon oxide, BF illumination is preferred. In order to detect a small particle on a surface, DF illumination generally yields better results.

In bright field illumination in general, the illumination is incident on the sample through the same objective lens as is used for viewing the sample. Reference is now made to FIG. 1, which shows a bright field illuminating laser source 300 delivering its output beam 15 into an optical delivery fiber bundle 21, preferably by means of a laser to fiber coupler 150. This optical fiber bundle 21 is required for the dual purposes of providing uniform illumination on the sample and for coherence breaking of the laser illumination, as will be expounded further hereinbelow. In the preferred embodiment of FIG. 1, only a single fiber bundle is used, but it is to be understood that a serial fiber bundle solution, as will be shown hereinbelow, could just as readily have been used. From the output termination of the fiber bundle 21, the laser beam is imaged by means of illumination transfer lenses 301, 302, onto the objective lens in use 201, which is operative to focus the illumination onto the wafer plane 100 being inspected. Appropriate alternative objective lenses 201' can be swung into place on an objective revolver 200, as is known in the microscope arts. The illumination returned from the wafer is collected by the same objective lens 201, and is deflected from the illumination path by means of a beam splitter 202, towards a second beam splitter 500, from where it is reflected through the imaging lens 203, which images the light from the wafer onto the detector 206. The second beam splitter 500 is used to separate the light going to the imaging functionality from the light used in the auto-focus functionality, which is directed by means of the auto-focus imaging lens 501 to the auto-focus detector 502.

When conventional dark field illumination is required for the imaging in hand, a dark field side illumination source 231 is used to project the required illumination beam 221 onto the wafer 100. When orthogonal dark field, or obscured reflectance dark field illumination is required for the imaging in hand, an alternative dark field illumination source 230 is used to project the required illumination beam 232 via the obscured reflectance mirror 240 onto the wafer 100 orthogonally from above.

A repetitively pulsed laser source is preferably used in the illumination system of the present invention, though according to other preferred embodiments, CW laser illumination may also be used. In accordance with the requirements of providing a high brightness light source that produces a directionally intense beam of short time duration and at high repetition rates, the third harmonic of a Nd:YAG Laser output is preferably used.

Speckle effects with CW lasers is comparatively easy to overcome, since it is possible to average the signal while varying the wave front. Several methods are described in the prior art for achieving this. When, however, the imaging process utilizes a single pulse for each acquired image, such a method becomes impossible to implement. According to further preferred embodiments of the present invention, there are provided methods whereby the coherence effect of the laser beam is reduced by splitting the laser beam into many beamlets and retarding each beamlet relative to the previous one in such a way that there is no definitive phase difference between them. The laser beam is thus divided into many parts, each part having no defined phase coherence with the other parts.

This requirement is insufficient, however, since it is also required that each point in the field of view (FOV) on the sample is illuminated by all parts of the laser beam. Each part of the beam is coherent or partially coherent with itself and thus may contribute to the generation of speckle, or to other interference effects that create high contrast artifacts in the image. Since each part of the beam is not coherent with the other parts of the beam, by ensuring that the FOV is illuminated by all parts of the laser beam, the total effect is averaged. The residual coherence effect depends on the number of beamlets used. Since each beamlet is independent of the others, the interference effect is reduced by the square root of the number of beamlets, assuming that all beamlets have the same intensity contribution. Consequently, the greater the number of beamlets, the lower the level of appearance of coherence artifacts in the image.

According to preferred methods of implementation of this technique, the laser beam is introduced into a fiber optics bundle, such as the fiber bundle 21 shown schematically in FIG. 1. The fibers in the bundle differ in length from each other by distances of the order of the laser coherence length in the fiber medium, or less. The number of fibers in the bundle dictates the contrast of the residual coherence effect in the image. The fiber bundle should preferably be illuminated uniformly. Each fiber in the bundle must carry more or less the same energy; otherwise averaging of the coherence effect will not be efficiently performed. Since the laser beam itself is not uniform and contains high and low spatial frequency components, the laser beam must be spatially mixed before introduction into the fiber. Additionally, the full numerical aperture of the fiber should preferably be filled, since at the far end of the bundle, uniform angular distribution of intensity is required. These latter two requirements do not appear to be fulfilled in the prior art. In the above-referenced article by Dingel et al., although it is stated that Koehler illumination is generated, no arrangement is shown for spatially mixing the laser beam, nor is there described a specific method for ensuring that the incident light is directed such that the Numerical Aperture of each fiber is fully illuminated. Under the conditions shown, each fiber would illuminate randomly, resulting in non-uniform field stop plane intensity, which then would also result in non-uniform illumination at the object plane. Furthermore, in the Dingle et al prior art, it is stated that the proposed array is made of N fiber-guides in which the length difference of any two fibers is greater than the coherence length of the light source. Such an arrangement would generally result in excessive differences, since it is the optical length difference and not the absolute length difference of any two fibers which needs to be greater than the coherence length of the light, according to the criteria chosen in the Dingel et al. article. Finally, the illumination system described in this prior art is for a transmissive imaging system.

An implementation of this method, according to a preferred embodiment of the present invention, is schematically illustrated in FIG. 2. The laser beam 15, which can be either a parallel beam or slightly convergent, or slightly divergent impinges onto a diffusing element 16, which, according to alternative and preferred embodiments, can be a regular diffuser, a holographic diffuser (such as an MEMS) or a micro-lens array having a numerical aperture that spreads the incident light at the required angles. The diffused beam, shown schematically in FIG. 2 by means of three exemplary rays 17 diffused at the same angle from different locations in the diffuser, is preferably imaged onto one point of the end face 20 of the terminal connector 19 of a fiber optics bundle 21 by means of a focusing element 18, which can be either a single lens, or, in order to reduce aberations, a multi-element lens. Rays diffused at different angles from those rays 17 shown in FIG. 2, are imaged onto different points of the end face 20 of the fiber optics bundle 21. Light from all of the included angles at which light is output from the diffuser is thus imaged by means of the focusing element 18 to cover the entire input aperture of the fiber bundle end face 20. The beam traverses the fiber bundle 21 and is output at the opposite end face 29 of the fibers at the output connector 22.

For optimum optical transfer efficiency, the diffusing element 16 is preferably positioned at the left focal plane of the focusing element 18, and the end face 20 of the fiber 21, at the right focal plane of the focusing element.

The half angle $\alpha$ of the diffusing element, and the focal length f, of focusing element are computed as follows:

"If r is the input beam radius and NA is the numerical aperture of the fiber, then NA=r/f by definition. Thus f=r/NA. Now, if R is the fiber bundle radius than $\alpha*f=R$. Thus, for a specific input beam diameter and fiber diameter, the focal length and the diffusing angle can be simply calculated."

The embodiments generally described in the prior art of the use of a fiber bundle to provide coherence breaking have disadvantages, relating to the effect of transmission losses in the fibers. In order to provide good coherence breaking, the difference in length between any pair of fibers of the bundle is described in the prior art as needing to be greater or equal to the coherence length of the light source. As a consequence, the difference in length between the fibers in the bundle is thus greater or equal to the coherence length times the number of fibers in the other bundle. Consequently, according to the criteria of the prior art, for a bundle containing hundreds or even thousands of fibers, there is an appreciable difference in length between the shortest and longest fibers of the bundle. This results in two disadvantageous effects in such prior art fiber bundles:

(i) Firstly, because of the transmission loses in typically used fiber materials, the light intensity output from each fiber of the bundle may be significantly different, falling with increasing fiber length. However, for the coherence breaking effect to be effective, there should ideally be only phase or time of flight differences between the various fiber outputs, and any differences in intensity contribution degrades the desired coherence breaking effect.

(ii) Secondly, the longer these differences in length, the longer the overall length of the bundle, and the longer the overall length of the bundle, the higher the transmission losses themselves, quite apart from their effect on the coherence breaking effects. These transmission losses make the illumination system inefficient and less cost-effective.

Figure 3A:
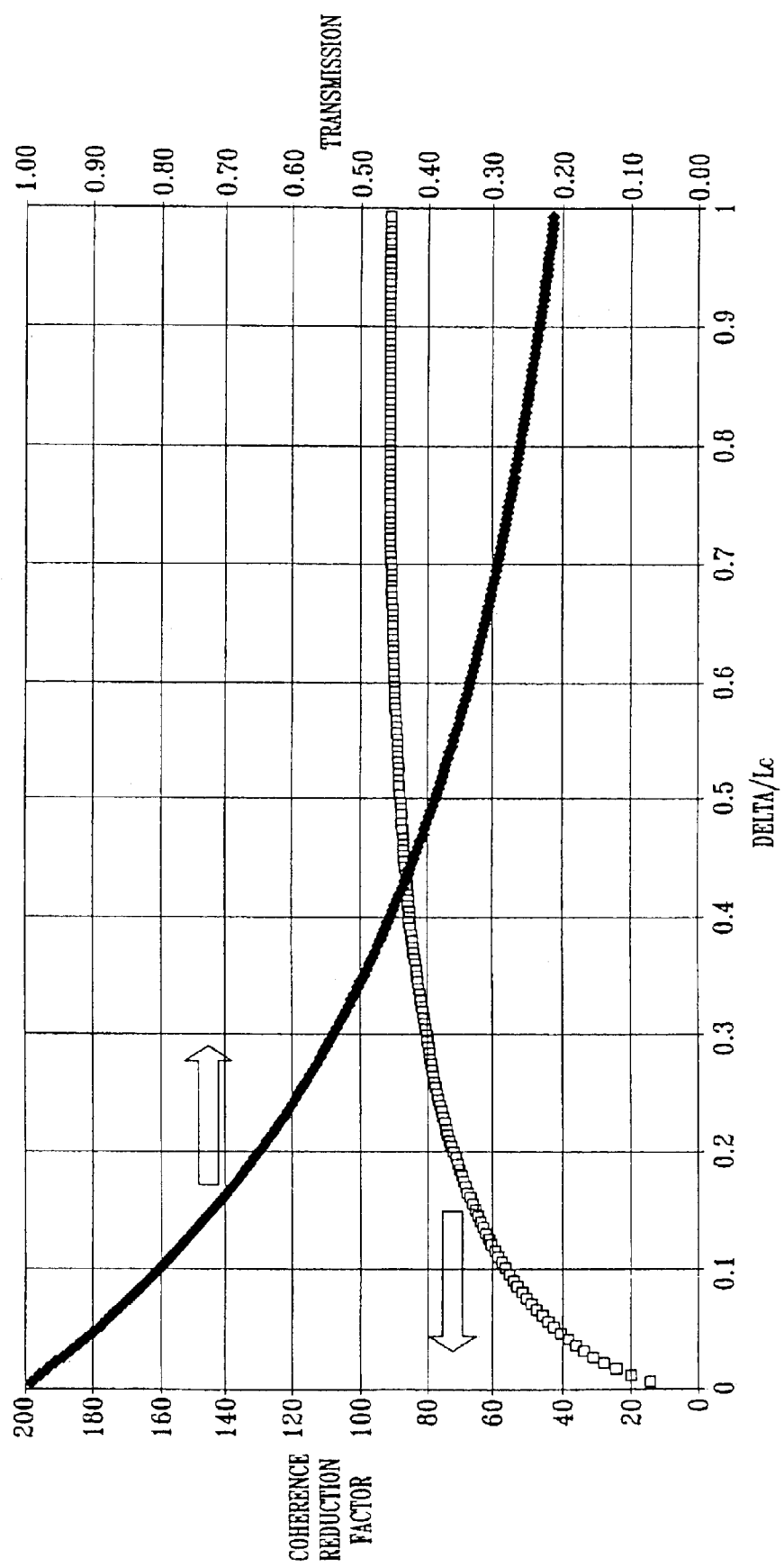

This effect can be illustrated by reference to FIG. 3A, which is a graphical illustration of the outcome of the above-described trade-off in fiber length difference between transmission and coherence breaking efficiency. The results shown in FIG. 3A are for a bundle containing 40,000 fibers, and for a fiber having a transmission loss in the UV of the order of 0.1 db/m. The two ordinates separately show the bundle transmission and the coherence reduction factor as a function of Delta/$L_C$, where each fiber differs in length by Delta mm., and the coherence length of the source is $L_C$. The transmission is measured relative to a bundle having uniform fiber lengths equal to the length of the shortest fiber in the variable fiber length bundle. The value of $L_C$ for the example shown is 5 mm.

"For such a 40,000 fiber bundle, the maximum theoretical coherence reduction factor is given by $(40,000)^{1/2}=200$. As is observed in the graph, for Delta/$L_c$=1, meaning that the fiber optical length differences are equal to the coherence length, the coherence reduction factor is approximately 90, compared to the maximum theoretical 200. It is to be noted that the coherence reduction factor falls short of its theoretical value because the increasing insertion loss of each successive fiber means that the intensity contribution of each separate fiber to the total output is not equal, and the coherence breaking effect is thus reduced. The transmittance of the bundle, on the other hand, has fallen to only 0.22 of that of a bundle with Delta/$L_c$=0, i.e. with no length differences, and such a transmission loss is serious."

If, on the other hand, the fiber optical length difference is reduced to only 0.4$L_C$, the coherence reduction factor is reduced to approximately 85, which is only a 6% reduction, while the transmission is increased to approximately 0.45, which is over a 110% increase.

According to these results, there is thus provided, according to a preferred embodiment of the present invention, an illumination delivery fiber bundle, operative for breaking the coherence of light transmitted therethrough, in which the differences in lengths of the fibers in the bundle are less than the coherence length of the source. Such a bundle, which compromises slightly on its coherence breaking properties by using fiber differences less than the coherence length, and thereby gains a substantial increase in illumination level, thus has significant economical advantages over the prior art bundles described above.

The above mentioned embodiments have been generally described in terms of typical pulsed laser sources, such as Nd:YAG lasers, where the coherence length is generally of the order of a few millimeters. It is evident that in systems using longer coherence length lasers, the problem is multiplied manyfold. Thus, for instance, a Helium-Neon CW laser typically has a coherence length of the order of 20 cm, under which conditions, the advantages of any of the various embodiments of the present invention become even more pronounced.

In order to improve the coherence breaking efficiency, it is known, for instance from the above-referenced U.S. Pat. No. 6,369,888, that it may be more economical to use two bundles with a smaller number of fibers in each, than one bundle with more fibers. If the fiber length differences in the first bundle exceeds the overall fiber length difference between the shortest and the longest fibers in the second bundle, then the effective number of fibers taking part in the coherence breaking process is the number of fibers in the first bundle times the number of fibers in the second bundle. This applies if the contribution of light to each fiber in the second bundle comes from all of the fibers in the first bundle.

Reference is now made to FIG. 3B, which is a schematic illustration of an optical arrangement for achieving this result, wherein a second bundle is provided serially with the first bundle of FIG. 2. From the exit end face 29 of the first bundle 21, three exemplary rays 23 propagating at the same angle from different locations in the end face 20, are shown being imaged onto the end face 26 of the fibers at the terminal connector 25 of the second fiber optics bundle 27 by means of a focusing element 24, which can be either a single lens, or a multi-element lens. The beam is output from the second fiber bundle 27 at the far end face 26 of the fibers at the output connector 28. It is not necessary that the diameter of the first bundle 21 be the same as the diameter of the second bundle 27, as shown in the preferred embodiment of FIG. 3B. If the first bundle has a smaller diameter, a diffuser is required at its end to increase the angular distribution of light from the end, in order to fill the input of the second bundle.

In the embodiment of the double fiber bundle arrangement described in U.S. Pat. No. 6,369,888, the fibers in both bundles are described as having different lengths, and the difference in length $\Delta L$ between any two fibers in one bundle is preferably selected to be greater than the coherence length of the light source. The difference in length between any pair in the other bundle is described as being, preferably larger than the difference in length between the shortest and the longest fiber in the first mentioned bundle.

However, in addition to the prior art disadvantage described above concerning the effect of the fiber length differences on the total intensity transmitted by the bundle, there is another disadvantage relating to the variation in intensity transmitted by the various fibers of the prior art double bundle embodiments. In order to provide good coherence breaking with a double bundle configuration, it is important that the phase-separated beamlets input to the second bundle, as generated by the different lengths of the fibers in the first bundle, should ideally be of equal intensity. Any departure from equal intensity results in degradation of the coherence breaking effect in the second bundle, since some of the differently phased output beams will be preferentially more intense than others, leading to a net residual coherence effect. In the above-mentioned Karpol et al patent, the difference in length between any pair of fibers in the first bundle is described as being preferably larger than the difference in length between the shortest and the longest fiber in the other bundle. The difference in length between any pair of fibers of that other bundle is described as being greater than the coherence length of the light source, such that the difference in length between the shortest and the longest fiber in the other bundle is thus greater than the coherence length of the light source times the number of fibers in the other bundle. The typical coherence lengths generated by lasers used for such applications are of the order of up to a few millimeters. Consequently, according to the criteria of this prior art, there is an appreciable difference in length between the fibers of the first bundle.

"There is therefore also a second trade-off between two effects, which oppositely affect the efficiency of the coherence breaking. On the one hand, the differences between the lengths of the fibers in the second bundle should preferably be more than the coherence length in order to generate efficient coherence breaking in such a bundle, and on the other hand, the larger the difference in lengths between the fibers anywhere in the double bundle embodiment, the more the coherence breaking in the second bundle is degraded because of lack of unity of intensity."

Furthermore, in the above-mentioned Karpol et al., prior art, it is stated that the difference in length ΔL between any two fibers in one bundle is preferably selected to be greater than the coherence length of the light source. This preferred difference in length is longer than the optical path length in the fiber by a factor N, where N is the refractive index of the core material, such that this method proposes use of a longer length difference between fibers than is dictated by optical considerations, even before any incentive to reduce fiber length differences, as discussed hereinabove.

Figure 3C:
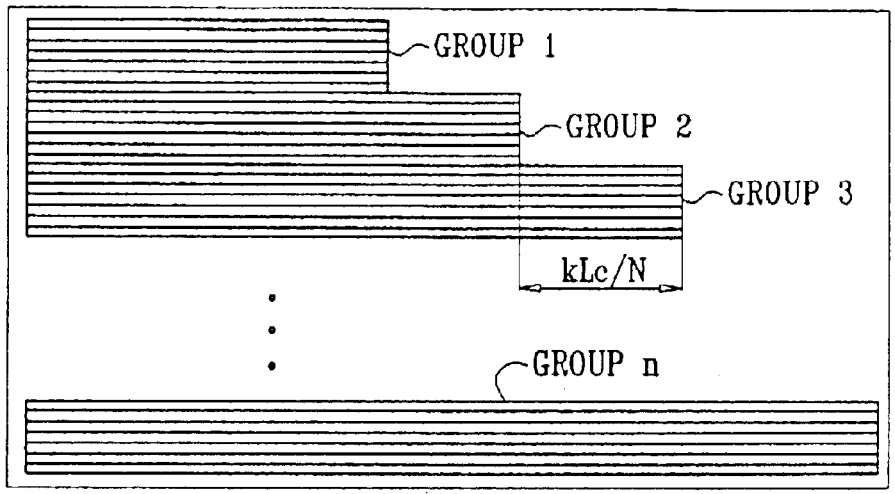
Figure 3D:
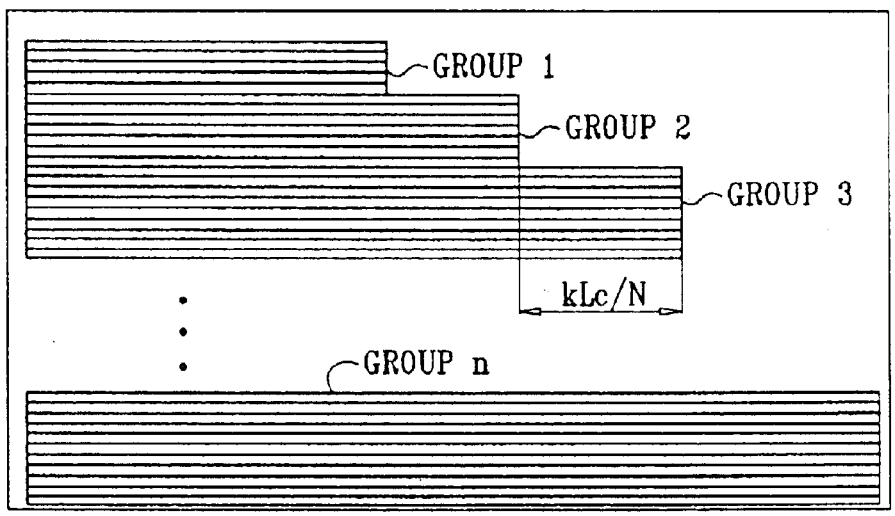
Figure 3E:
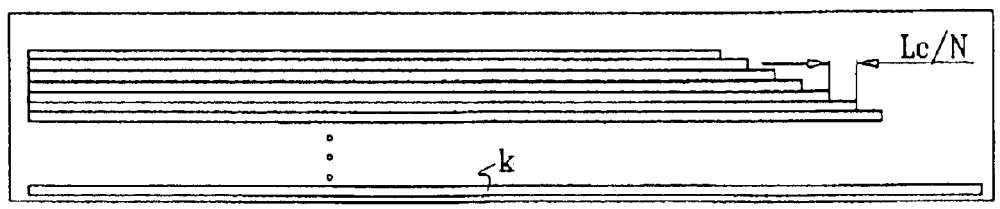

"Reference is now made to FIGS. 3C and 3E, which respectively illustrate schematically the two bundles of a double fiber bundle delivery system, constructed and operative according to another preferred embodiment of the present invention. This embodiment is operative to diminish the above-described disadvantages of the prior art double fiber bundle delivery system. For the purposes of explaining the operation of this embodiment, the fiber bundle shown in FIG. 3C is regarded as the input bundle, denoted 21 in the embodiment of FIG. 3B, and the fiber bundle shown in FIG. 3E is regarded as the output bundle, denoted 27 in FIG. 3B, though it is to be understood that this embodiment is equally operable with the fibers in either order, if the correct matching components are provided."

Considering now the first bundle, in order to generate good coherence breaking, every fiber should optimally be of a different optical length by the sum of all of the optical length differences of the fibers in the second bundle. On the other hand, in order to avoid intensity variation effects from degrading the coherence breaking effect of the second bundle, equal optical length fibers should ideally be used, but this would generate no coherence breaking in the first bundle. There is therefore provided, in accordance with a preferred embodiment of the present invention, and as illustrated in FIG. 3C, a compromise bundle construction, in which the fibers are divided into groups, each group containing fibers of the same optical length, and each group preferably being different in optical length from another group in the bundle by the sum of all of the optical length differences of the fibers in the second bundle. In the embodiment of FIG. 3C, therefore, the fibers within each group provide an element of uniformity to the beamlets output from the first bundle, while the difference in optical lengths between the groups provides the coherence breaking properties of the light from the different groups. The correct trade-off between these two effects is able to compensate to a large extent for the reduction in efficiency from the coherence breaking effect that would be obtained if all the fibers were of different optical lengths, but were also loss free, such that the intensity change effect was not a factor. The extent of the compensation between these two effects is a function of the attenuation per unit length of the fiber used.

According to yet another preferred embodiment of the present invention, instead of each group having the same number of fibers, as a result of which, the longer groups still have a lower light output than the shorter groups, it is possible to ensure that each group has the same transmitted intensity by varying the number of fibers in each group. Reference is now made to FIG. 3D, which is a schematic drawing of a bundle of fibers, according to yet another preferred embodiment of the present invention, similar to that shown in FIG. 3C, but in which the number of fibers in each group is increased according to the length of the group. Even more preferably, the number of fibers in each group is made generally proportional to the length of the group. In this way, the increased insertion loss arising in a group because of the additional fiber length in the group is offset by the increase in the number of fibers in that group.

A further advantage in the use of groups of fibers, according to this embodiment of the present invention, is that the redundancy effect of a large number of fibers operating in parallel has the effect of smoothing out any production differences which inevitably arise between supposedly identical fibers both in optical properties and in targeted cleaved length.

Reference is now made to FIG. 3E, which is a schematic drawing of the second bundle of fibers, according to this preferred embodiment of the present invention. In the second bundle, each of the fibers is preferably of a different optical length, the optical lengths preferably differing by the coherence length of the light source or less. Since the total overall difference in optical lengths of the Fibers in the second bundle is determinative in fixing the difference in the optical lengths between the different groups of fibers in the first bundle, and as mentioned above, there is an advantage in keeping the path differences between fibers as short as possible to minimize intensity changes between fibers or fiber groups, there is an additional advantage to the first bundle parameters if the optical lengths of the fibers in the second bundle differ by as little as possible. For this reason, preferred use of fiber optical lengths differing by less than the coherence length of the light source can be advantageous in the second bundle, commensurate with achieving sufficient coherence breakage in the combination. The determination of how much less than the coherence length to use in a particular beam delivery system is ascertained according to the attenuation constant of the fibers used in the bundles, and in accordance with the above-described trade-off considerations.

According to the above mentioned preferred embodiments of the present invention, there is described a system comprising only one bundle of the type containing the groups of fibers, whether that bundle is positioned in front of or after the bundle containing the single fibers. According to more preferred embodiments of the present invention, in series with the bundle containing the single generally ungrouped fibers, a plurality of bundles with groups of fibers can be used, instead of a single such bundle, such that the illumination system comprises a series of bundles of fibers, with the groups of fibers and the fibers respectively optimally arranged for good coherence breaking properties and minimal transmission losses, as expounded hereinabove.

Some examples are now provided to illustrate one preferred embodiment of FIGS. 3C to 3E quantitatively. Reference is first made to the second bundle, as shown in FIG. 3E, which has k fibers, where k is preferably of the order of 1000. The length of a first fiber is L, where L is preferably of the order of 1 meter. A second fiber is longer than the first by $L_c/N$, where $L_c$ is the coherence length of the laser source, typically 6 mm, and N is the fiber core refractive index, generally of the order of 1.5, such that the fiber length difference is of the order of 4 mm. A third fiber is longer than the second also by $L_c/N$, and so on. The sum of all k length differences is thus $k \times L_c/N$, which amounts to the order of 4 meters for this preferred example.

The first bundle, as in FIG. 3C, has a number n of groups of fibers, where n is preferably 10 to 20. Each group contains m, preferably 20 to 50, fibers of equal length and equal optical path length. The length difference between each of the groups is equal to or greater than the sum of all of the length differences of the second bundle, which, in this preferred example, amounts to approximately 4 meters, as obtained above. From these numerical examples, the reason for limiting differences in fiber lengths to limit transmission loss changes, becomes evident.

The above-described embodiments of the present invention for achieving beam coherence breaking also result in a solution for a problem related to the use of short pulsed lasers in such illumination systems. Such short laser pulses, which can typically be as short as only a few nanoseconds, may have a peak power density so high that the focussed beam may cause damage to the wafer under inspection. A common method used to decrease the peak power of a short laser pulse is to stretch the pulse, such that the pulse energy is expended over a longer time, and hence has a lower peak power. Such pulse stretching can be performed by transmitting the pulse in parallel down several paths of different optical path length, and recombining after transit. This is the situation which exists with the assembly of variable length fibers in the bundles shown in the embodiments of FIGS. 2 and 3A–3E of the present invention, such that the fiber bundles of the present invention are also effective in pulse stretching applications.

To illustrate this application of the preferred embodiments of the present invention, the above mentioned numerical example will be used. For the preferred bundle having 20 groups, each different in length by 4 meters, a total length difference of 80 meters is generated. The time of flight of light in the medium of the fiber, having a refractive index of 1.5, is approximately 5 nsec/meter. Thus the total time of flight difference for an 80 meter bundle is approximately 400 nsec. The effect of the bundle is thus to generate pulse stretching from the typically few nanosecond pulse lengths emitted by the laser, to about two orders of magnitude longer, with the concomitant reduction in potential beam damage. For at least one bundle some or all of the optical path differences between fibers is less than the beam coherence length.

A particular feature of a preferred embodiment of the present invention is that the system includes a second fiber optic bundle, within which the optical path length difference between each pair of fibers is less than or equal to the coherence length of the light beam being employed by the system.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. An optical system for reducing the coherence of a beam for illumination of an object, comprising:

a source of at least partially coherent illumination, at least part of said illumination having a characteristic coherence length;

a first fiber optics bundle comprising a plurality of optical fibers, at least some of which have differing optical lengths, at least some of said fibers of differing optical length having differences in optical lengths therebetween which are less than said characteristic coherence length; and at least a second fiber optics bundle disposed serially with said first bundle, comprising a plurality of groups of optical fibers, each group of fibers comprising fibers of essentially the same length, and wherein at least some of said group of fibers have differing optical lengths, at least some of said groups of fibers having differences in optical lengths therebetween which are at least equal to the sum of all of the optical length differences of said fibers in said first bundle.

2. An optical system according to claim 1 and wherein said at least a second fiber optics bundle comprises a plurality of serially disposed fiber optics bundles, each comprising a plurality of groups of optical fibers.

3. An optical system according to claim 1 and wherein each of said groups comprises essentially the same number of fibers.

4. An optical system according to claim 1 and wherein the number of fibers in each of said groups increases according to the optical length of said group.

5. An optical system according to claim 4 and wherein the number of fibers in each group is generally proportional to the length of said group.

6. An optical system according to claim 1 and wherein said bundles are arranged serially such that said beam for illumination of said object is initially incident on said first bundle.

7. An optical system according to claim 6 and wherein each of said first bundle and said second bundle have an input and an output;

and also comprising an optical element positioned between said first bundle and said second bundle such that it is operative to direct illumination from any point of said output of said first bundle onto essentially each point of said input of said second bundle.

8. An optical system according to claim 1 and wherein said bundles are arranged serially such that said beam for illumination of an object is initially incident on said second bundle.

9. An optical system according to claim 8 and wherein each of said first bundle and said second bundle have an input and an output;

and also comprising an optical element positioned between said second bundle and said first bundle such that it is operative to direct illumination from any point of said output of said second bundle onto essentially each point of said input of said first bundle.

10. An optical system according to claim 1 and wherein said source of at least partially coherent illumination is a laser source.

11. An optical system according to claim 1 and wherein said at least partially coherent illumination has at least one of spatial coherence and temporal coherence.

12. An optical system according to claim 11 and wherein said plurality of optical fibers in said first fiber optics bundle are randomly ordered, such that said spatial coherence is reduced.

13. An optical system according to claim 1 and also comprising a diffusing element for spatial mixing of said beam.

14. An optical system according to claim 1 and wherein said differences in optical lengths of some of said plurality of optical fibers in said first bundle, being less than said characteristic coherence length, reduces transmission losses in said system.

* * * * *